United States Patent [19]

Varon

[11] Patent Number: 5,377,841

[45] Date of Patent: * Jan. 3, 1995

[54] SLEEP THERAPY PACKAGE

[75] Inventor: Steven C. Varon, Neshanic Station, N.J.

[73] Assignee: Carter-Wallace, Inc., New York, N.Y.

[*] Notice: The portion of the term of this patent subsequent to Oct. 4, 2011 has been disclaimed.

[21] Appl. No.: 165,386

[22] Filed: Dec. 10, 1993

[51] Int. Cl.⁶ .............. B65D 71/00; B65D 85/672; B65D 85/42
[52] U.S. Cl. .............. 206/570; 206/232; 206/538; 206/387.1; 434/308
[58] Field of Search .............. 206/570, 232, 528, 534, 206/538, 387; 434/309, 311, 308

[56] References Cited

U.S. PATENT DOCUMENTS

| | | | |
|---|---|---|---|
| 2,877,893 | 3/1959 | Volcheming et al. | 206/232 |
| 3,076,541 | 2/1963 | Volcheming | 206/232 |
| 3,207,301 | 9/1965 | Sparks | 206/232 |
| 3,225,913 | 12/1965 | Lee | 206/534 X |
| 3,302,776 | 2/1967 | Sparks | 206/564 X |
| 3,302,777 | 2/1967 | Sparks | 206/564 X |
| 3,803,728 | 4/1974 | Scott | 434/308 |
| 3,934,226 | 1/1976 | Stone et al. | 434/308 X |
| 4,189,053 | 2/1980 | Stagnitto et al. | |
| 4,255,872 | 3/1981 | Williams, Sr. | 434/308 |
| 4,889,238 | 12/1989 | Batchelor | |
| 4,925,033 | 5/1990 | Stoner | |
| 4,958,736 | 9/1990 | Urheim | 206/538 X |
| 5,022,522 | 6/1991 | Kennedy | |
| 5,046,609 | 9/1991 | Mangini et al. | |
| 5,103,972 | 4/1992 | Ackeret | |
| 5,291,191 | 3/1994 | Moore | 221/3 X |

FOREIGN PATENT DOCUMENTS 3013878 10/1981 Germany .............. 206/232

Primary Examiner—Bryon P. Gehman
Attorney, Agent, or Firm—Watov & Kipnes

[57] ABSTRACT

A package for sleep therapy including a box having cards with doses in the form of tablets or capsules thereon, some of which are sleep inducing medicine and some of which are placebos, and an audiogenic recording for inducing sleep.

4 Claims, 2 Drawing Sheets

SLEEP THERAPY PACKAGE

RELATED APPLICATION

The present invention is related to that of co-pending application Ser. No. 08/165,385, entitled "Sleep Therapy Package" filed on the same date herewith, now U.S. Pat. No. 5,351,819.

FIELD OF THE INVENTION

The present invention relates generally to the field of product packaging, and more particularly to the packaging of sleep therapy systems.

BACKGROUND OF THE INVENTION

Various ways have been used over the years to induce sleep. Some of them use medicine and others play back audiogenic recordings of soothing music or of sounds with peaceful connotations such as surf or a beach.

SUMMARY OF THE INVENTION

In accordance with this invention, a package is provided that contains an audiogenic recording designed to induce sleep and a supply of capsules or pills to be taken as instructed. Most of the capsules or pills contain sleep inducing medicine but some contain a placebo in order to reduce any tendency for a user to develop a dependency on the medicine.

BRIEF DESCRIPTION OF THE DRAWINGS

Various embodiments of the present invention are described below with reference to the drawings, wherein similar items are identified by the same reference designation, in which.

DETAILED DESCRIPTION OF THE PREFERRED EMBODIMENTS OF THE INVENTION

Figure 1:
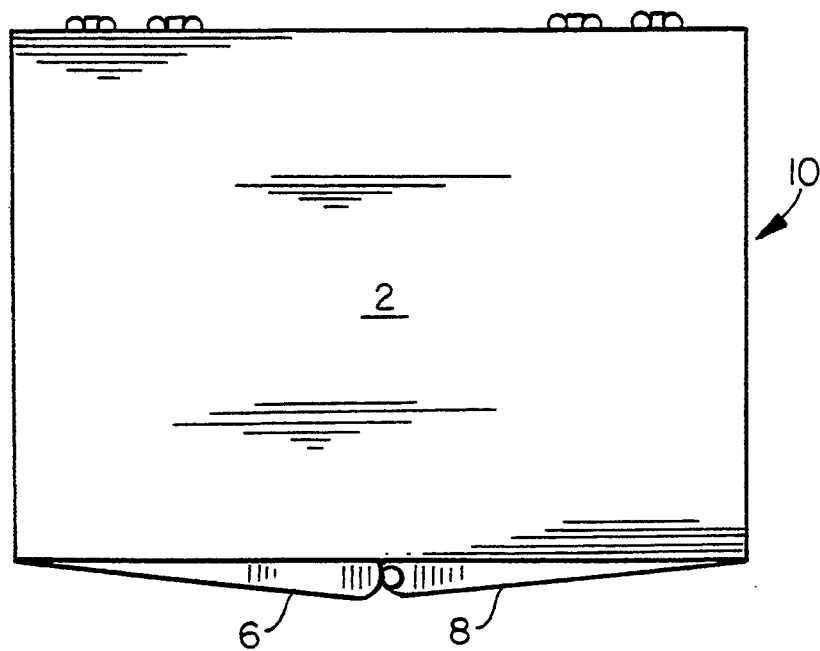
FIG. 1 is a top view of a closed package of this invention.
Figure 3:
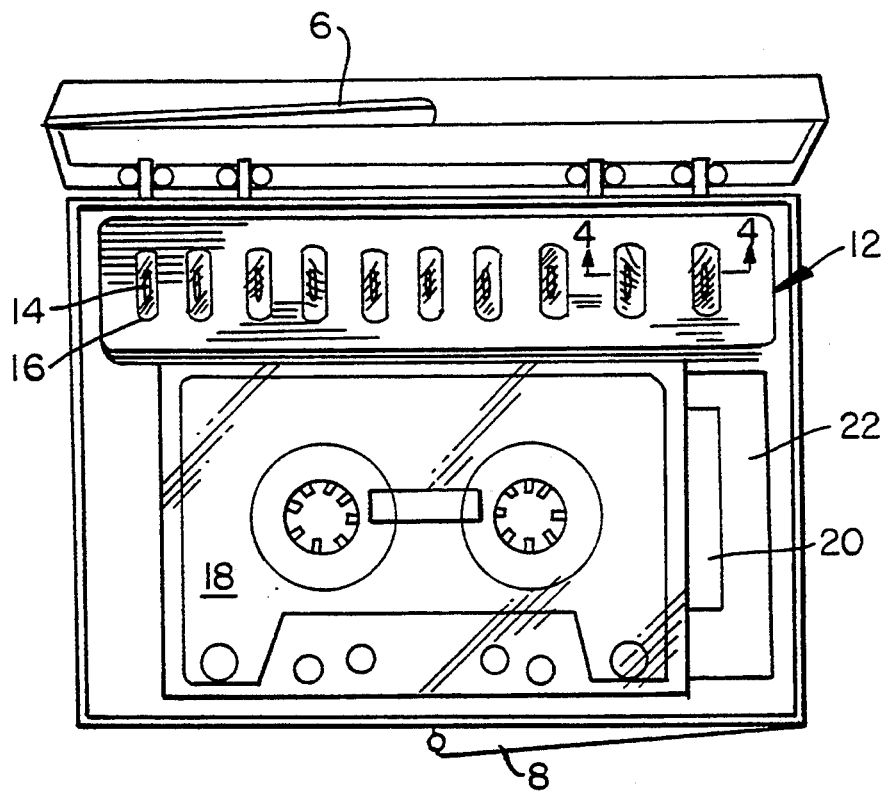
FIG. 3 is a top view of an open package of this invention.
Figure 2:
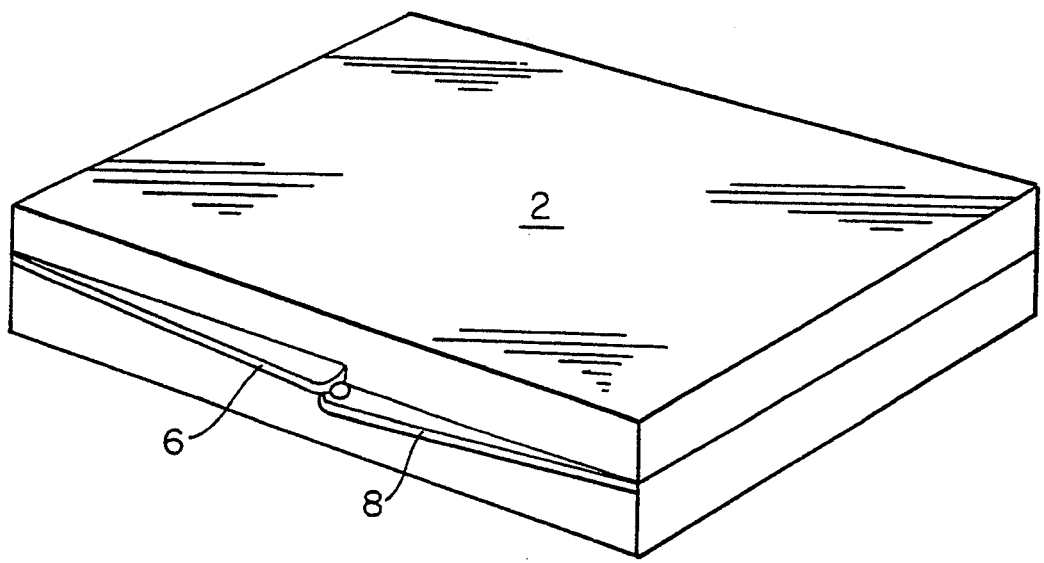
FIG. 2 is a pictorial view of the package.

In FIGS. 1 and 2 a cover 2 and closing snaps 6 and 8 of a box 10 for a package containing items for inducing sleep are shown. When the cover 2 is open, as in FIG. 3, it is seen that the package contains a card 12 having medicinal doses in the form of capsules or tablets 14 mounted thereon in any suitable manner such as, for example, in blister cells 16. Although only ten doses are shown, it is preferable that the card 12 have enough doses for a thirty day supply. It is important in accordance with this invention that some of the doses be placebos in order to reduce any tendency for the medicine becoming habit forming.

An important element of the package is an audiogenic tape 18 having program material recorded thereon that is designed to induce sleep.

In order to comply with laws, the package includes statements and warnings in written material 20 related to the medicine involved.

In addition, the package includes instruction sheets 22 on how to conduct the sleep inducing program, such as when to play the recording and the timing of the taking of the doses or tablets 14, as well as other procedures calculated to induce sleep.

Figure 4:
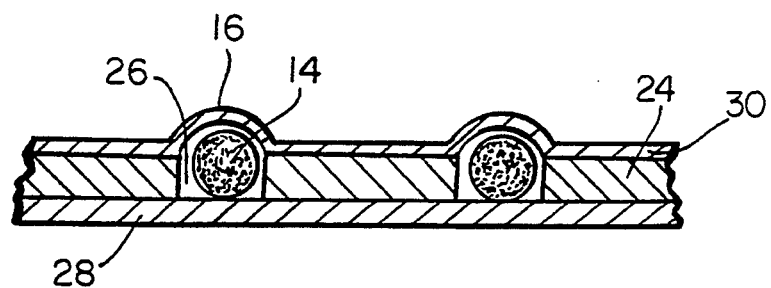
FIG. 4 is a cross-section taken along 4—4 of FIG. 3 of a strip of capsules or pills of sleep inducing medicine, some of which are placebos.

FIG. 4 is a cross-section 4,4 of the card 12. A sheet 24 of cardboard has holes 26 therein at the locations of the blisters 16 of FIG. 3. A sheet 28 of easily ruptured material such as a metal foil is adhered to the bottom of the sheet 24, and the doses 14 in the form of tablets or capsules are then placed in the holes 26 so as to rest on the sheet 28. Then a flexible sheet 30 having the blisters (humps) 16 is adhered to the sheet 24. A dose 14, whether it be in capsule or tablet form, is obtained by pushing on the related blister 16 with sufficient force to cause the dose 14 to rupture the foil sheet 28.

A set of written instructions for the sleep inducing program, is as follows:

1. Take DORAL ® Tablets, as directed by your doctor, until your supply runs out. This will be one tablet each night at a specified time before you go to bed.
2. After taking a DORAL ® Tablet, listen to the audio relaxation cassette while lying in bed.
3. Follow the tips on how to create a restful sleep environment.
4. Continue listening to the audio relaxation cassette for at least 5 days after your supply of DORAL ® Tablets is finished.
5. Before starting therapy, complete questions 1 to 3 of the questionnaire; complete question 4 after 3 days of therapy; and complete questions 5 to 14 five days after completing the DORAL ® Tablets component of the program.
6. Return the top part to your doctor and mail the bottom two copies to the address printed on the questionnaire.

Although various embodiments of the invention have been shown and described herein, they are not meant to be limiting. Those of skill in the art may recognize certain modifications to these embodiments, which modifications are meant to be covered by the spirit and scope of the appended claims.

What is claimed is:

1. A sleep therapy package comprising:
   a box having a cover;
   an audio recording of program material within said box for inducing sleep;
   a card having removably mounted thereon a plurality of doses, some of which are a medicine for inducing sleep and at least one of which is a placebo;
   patient instructions within said box setting forth material required by law for said medicine; and
   instructions within said box for the use of said doses and said recording for inducing sleep.
2. A sleep therapy package as set forth in claim 1, wherein said doses are contained within blisters.
3. A sleep therapy package as set forth in claim 1, wherein said doses consist of tablets.
4. A sleep therapy package as set forth in claim 1, wherein said doses consist of capsules.

* * * * *